(12) United States Patent
Richardson

(10) Patent No.: US 8,449,611 B2
(45) Date of Patent: May 28, 2013

(54) INTRAOCULAR LENS

(75) Inventor: Gary A. Richardson, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 191 days.

(21) Appl. No.: 12/752,466

(22) Filed: Apr. 1, 2010

(65) Prior Publication Data

US 2011/0245920 A1 Oct. 6, 2011

(51) Int. Cl.
*A61F 2/16* (2006.01)

(52) U.S. Cl.
USPC .......................................... 623/6.43

(58) Field of Classification Search
USPC .............. 623/6.11, 6.38–6.43, 6.46
See application file for complete search history.

(56) References Cited

U.S. PATENT DOCUMENTS

| | | | |
|---|---|---|---|
| 571,640 A | 2/1998 | Tran et al. | |
| 6,051,025 A * | 4/2000 | Ortuno et al. | 623/6.11 |
| 7,621,949 B2 * | 11/2009 | Deacon et al. | 623/6.49 |
| 7,883,540 B2 * | 2/2011 | Niwa et al. | 623/6.13 |
| 2008/0109077 A1 * | 5/2008 | Bos | 623/6.43 |
| 2010/0145446 A1 | 6/2010 | Shoji et al. | |

FOREIGN PATENT DOCUMENTS

| | | |
|---|---|---|
| DE | 102008006174 A1 | 7/2009 |
| EP | 2060242 A1 | 5/2009 |
| EP | 2305177 A1 | 4/2011 |
| FR | 2773705 A1 | 7/1999 |
| FR | 2790661 A1 | 9/2000 |
| JP | 2008220863 | 9/2008 |
| WO | WO 2005099631 A2 | 10/2005 |
| WO | WO 2009153873 A1 | 12/2009 |
| WO | WO 2010095628 A1 | 8/2010 |

* cited by examiner

*Primary Examiner* — William H Matthews
(74) *Attorney, Agent, or Firm* — Joseph Barrera

(57) ABSTRACT

An intraocular lens comprises an optic portion having a peripheral edge and at least two haptics. Each haptic is integrated with the peripheral edge of the optic portion by a corresponding haptic integration region. Also, each haptic comprises a distal segment region and a deformation segment region. The distal segment region has an outer distal length bounded by a proximate endpoint and a distal endpoint on an outer surface of the haptic, and is scribed by a distal segment angle $\alpha$ of 20° to 30°. The distal segment angle has a segment origin that lies within a radial segment bound by a radial distance 1.5 mm to 1.9 mm from an optic center and a segment angle $\theta$ of from 30° to 45° from a vertical axis. The vertical axis extends through the distal endpoint of at least one haptic and the optic center.

23 Claims, 10 Drawing Sheets

INTRAOCULAR LENS

FIELD OF THE INVENTION

The invention is directed to an intraocular lens, and in particular, an intraocular lens with haptics designed to provide positional stabilization of the lens in the lenticular capsular bag.

BACKGROUND OF THE INVENTION

A common and desirable method of treating a cataract eye is to remove the clouded, natural lens and replace it with an artificial intraocular lens (IOL) in a surgical procedure known as cataract extraction. In the extracapsular extraction method, the natural lens is removed from the lenticular capsular bag while leaving the posterior part of the capsular bag (and preferably at least part of the anterior part of the capsular bag) in place within the eye. In this instance, the lenticular capsular bag remains anchored to the eye's ciliary body through the zonular fibers. The capsular bag also continues its function of providing a natural barrier between the aqueous humor at the front of the eye and the vitreous humor at the rear of the eye.

Another trend in modern day cataract surgery is the reduction of the corneal incision size because larger incision sizes have been attributed to unwanted post-surgical conditions such as incision-induced astigmatism. IOLs and IOL inserters capable of successfully inserting the IOL through a sub 2.5-mm incision is desired by most cataract surgeons. Because the IOL undergos compression and other forces as it is passed through the IOL inserter, the dimensions (particularly the cross-section) of the IOL must accordingly be minimized. An IOL designer is thus further challenged in making an IOL that will have the strength and stability to remain centered in the eye, yet has a dimensional size and mechanical flexibility at near room temperature to pass through a sub-2.5 mm incision size. It will be appreciated that these are often competing design goals in that reducing IOL dimensions to fit within a smaller incision can result in a decrease in the strength and stability of the IOL in the eye.

The strength and stability of the IOL within the eye is of course crucial in obtaining and maintaining the intended vision correction expected by the physician and, more importantly, the patient. Accordingly, there remains a need for an improved IOL design that is dimensioned to fit through a sub-2.5 mm incision, and yet, is positionally stable in the capsular bag for many years following the surgery. It is also, important to the physician that the IOL have the ability to self-center within the capsular bag to minimize the amount of physical manipulation of the lens following insertion of the lens.

SUMMARY OF THE INVENTION

An intraocular lens comprises an optic portion having a peripheral edge and at least two haptics. Each haptic is integrated with the peripheral edge of the optic portion by a corresponding haptic integration region. Also, each haptic comprises a distal segment region and a deformation segment region. The distal segment region has an outer distal length bounded by a proximate endpoint and a distal endpoint on an outer surface of the haptic, and is scribed by a distal segment angle $\alpha$ of 20° to 30°. The distal segment angle has a segment origin that lies within a radial segment bound by a radial distance 1.5 mm to 1.9 mm from an optic center and a segment angle $\theta$ of from 30° to 45° from a vertical axis. The vertical axis extends through the distal endpoint of at least one haptic and the optic center.

One embodiment is directed to an intraocular lens comprising an optic portion and two haptics, and each haptic is integrated to a peripheral edge of the optic portion by a haptic integration region. The optic portion, the two haptics and the haptic integration regions are each formed of a hydrophobic polymeric material having a tangent modulus of elasticity of 2 MPa to 6 MPa. Each of the haptics comprise a distal segment region and a deformation segment region. The distal segment region has an outer distal length bounded by a proximate and a distal endpoint on an outer surface of the haptic, and is scribed by a distal segment angle $\alpha$ of 20° to 30°. The distal segment angle has a segment origin that extends a radial distance of 1.5 mm to 1.9 mm from an optic center and a segment angle $\theta$ of from 34° to 40° from a vertical axis. The vertical axis extends through the distal endpoint of at least one of the two haptics and the optic center. The deformation segment region has an outer deformation length bounded by a proximate deformation endpoint on an outer surface and the proximate endpoint of the corresponding distal segment region, and is scribed by a deformation segment angle $\beta$ of 20° to 40° from the segment origin.

Another embodiment is directed to an intraocular lens comprising an optic portion and at least two haptics. Each haptic is integrated to a peripheral edge of the optic portion by a haptic integration region, and each of the haptics comprise a distal segment region and a deformation segment region. A portion of the distal segment region and a portion of the deformation segment region combine to form an angle of contact of not less than 50° and not more than 70° when the haptics are diametrically stressed with an arcuate jaw according to ISO Test No. 11979-3(2006), which models a lenticular capsular bag of a human eye.

BRIEF DESCRIPTION OF THE DRAWINGS

Illustrative, non-limiting embodiments of the present invention will be described by way of example with reference to the accompanying drawings, and in which.

DETAILED DESCRIPTION OF THE INVENTION

Figure 1:
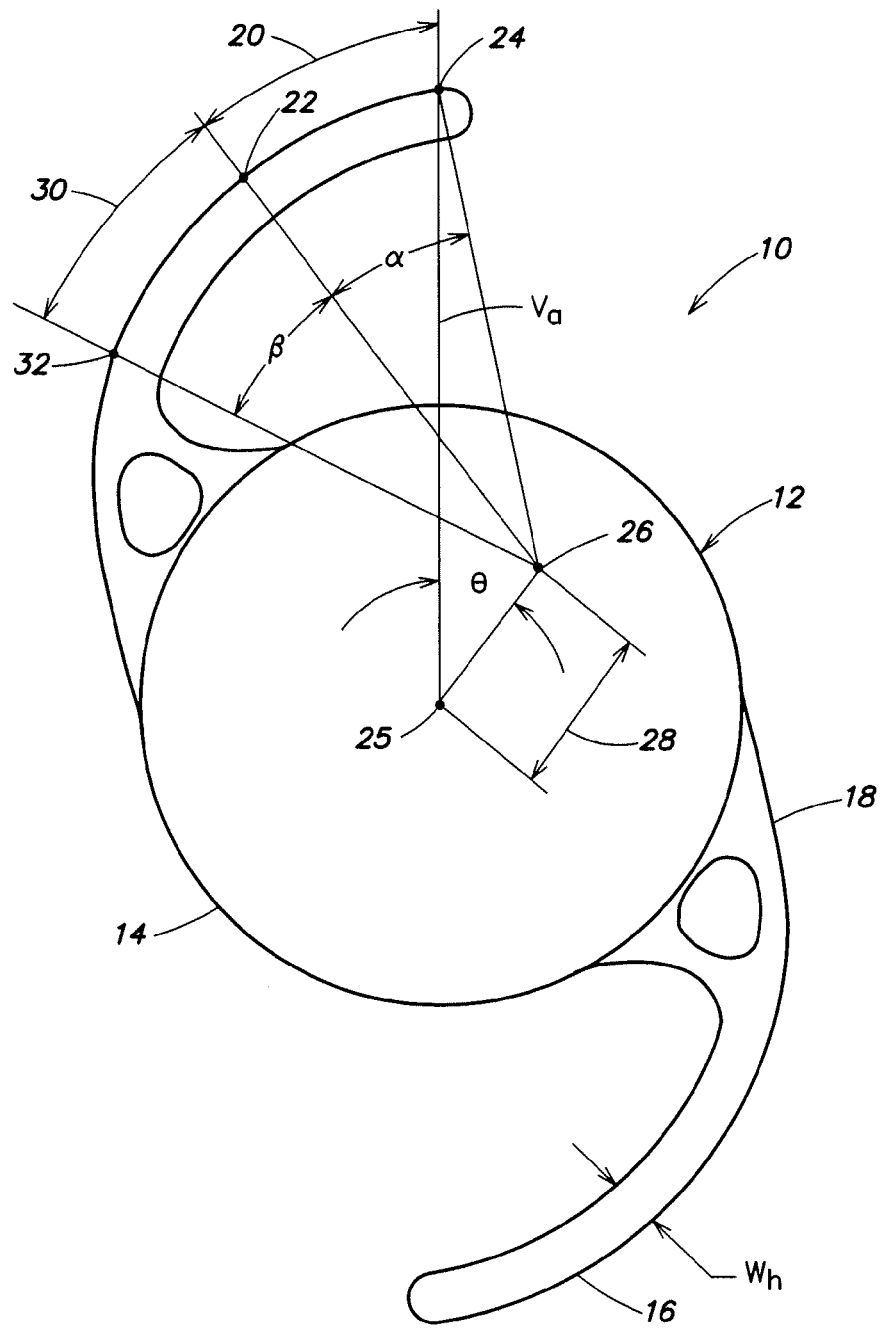
FIG. 1 is a representation of an IOL of the invention.

As shown in FIG. 1 an intraocular lens 10 includes an optic portion 12 having a peripheral edge 14 and at least two haptics 16, and each haptic 16 is integrated with the peripheral edge of the optic portion by a corresponding haptic integration region 18. Each haptic 16 includes a distal segment region 20 and a deformation segment region 30. The distal segment region 20 has an outer distal length bound by a proximate endpoint 22 and a distal endpoint 24. The distal segment region 20 is scribed by a distal segment angle α of 20° to 30° having a segment origin 26 that lies within a radial segment bound by a radial distance 28 of 1.5 mm to 1.9 mm from an optic center 25 and a segment angle θ of from 30° to 45° from a vertical axis. As shown, the vertical axis $V_a$ extends through the distal endpoint 24 of at least one haptic 16 and the optic center 25. As stated, the intraocular lens 10 also includes a deformation segment region 30 that has an outer deformation length bounded by a proximate deformation endpoint 32 and the proximate endpoint 22 of the distal segment region 20. The deformation segment region 30 is scribed by a deformation segment angle β of 20° to 40° from the segment origin 26.

As stated, the at least two haptics 16 are integrated with the peripheral edge 14 of the optic portion 12. The term "integrated" means that the haptics 16 can be formed with the optic portion 12 as a one-piece IOL. As an example, the IOL can be formed from a polymeric button. The polymeric button is then lathed to the exterior geometric shape of the IOL including the optic portion and haptics from a single polymeric material. The term "integrated" also means that the haptics 16 and optic portion 12 can be formed of different polymeric materials and then subsequently joined at the peripheral edge 14 of the optic portion 12. As an example, an IOL with an optic portion and two separately formed haptics that are subsequently joined is referred to in the art as a three-piece IOL. Accordingly, one of ordinary skill in the art understands the term "integrated" as referring to either a one-piece IOL formed and shaped from a single polymeric material or a multiple piece IOL in which the haptics are joined or attached to the optic, e.g., a three-piece IOL, as just described.

If the IOL is not formed or lathed from a single polymeric material the haptics can be joined to the optic portion by methods known in the art, for example as described in U.S. Pat. No. 5,217,491 to Vanderbilt. In some instances, three piece IOLs can provide additional functional design considerations. Typically, to facilitate movement or warping of the optic portion in response to the relaxation or the contraction of the ciliary muscle body in the eye, and therefore, in principle, provide a degree of lens accommodation, one can design an IOL with different polymeric materials. The design choice often involves the selection of a relatively stiff polymer for the haptics, e.g., a polyimide, and a relatively soft or compressible polymer for the optic portion.

Figure 2A:
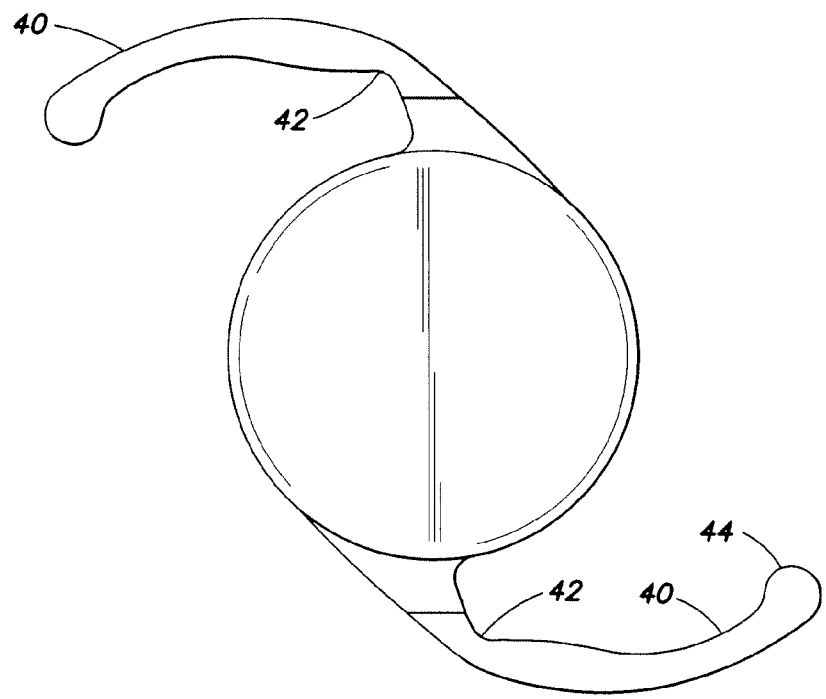
FIG. 2A is a representation of an IOL in the prior art.
Figure 2B:
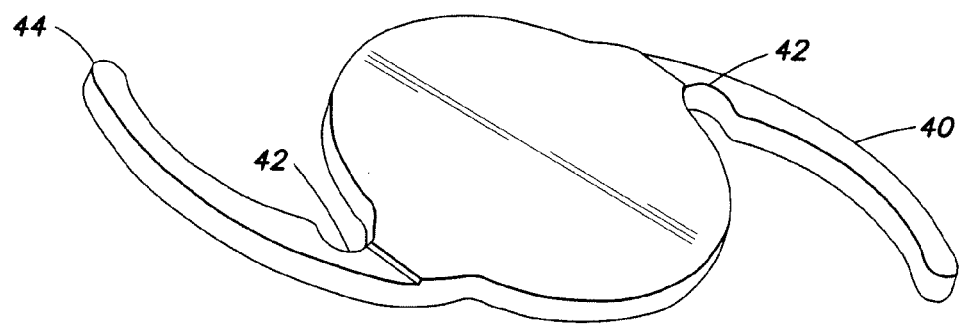
FIG. 2B is a representation of an IOL in the prior art.
Figure 9:
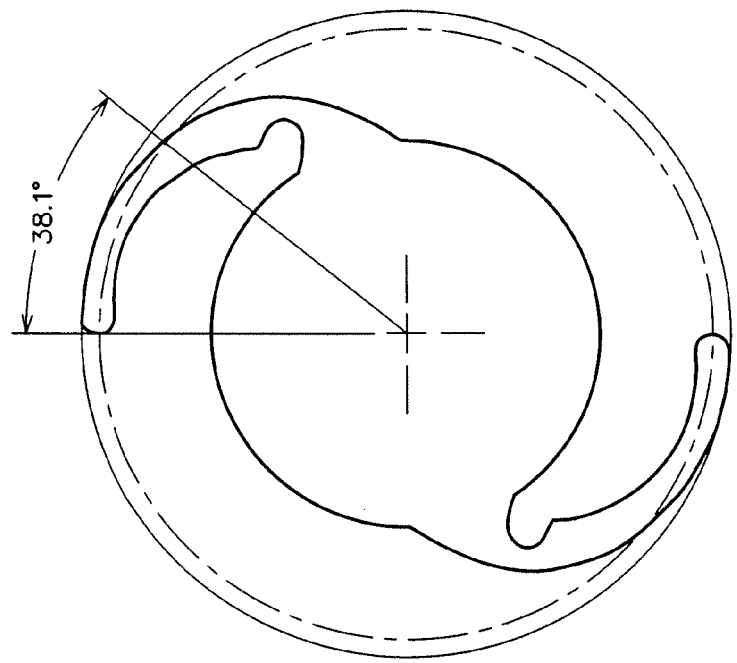
FIG. 9 is a model representation of the prior art IOL of FIG. 2B in a capsular bag and the angle of contact.
Figure 8:
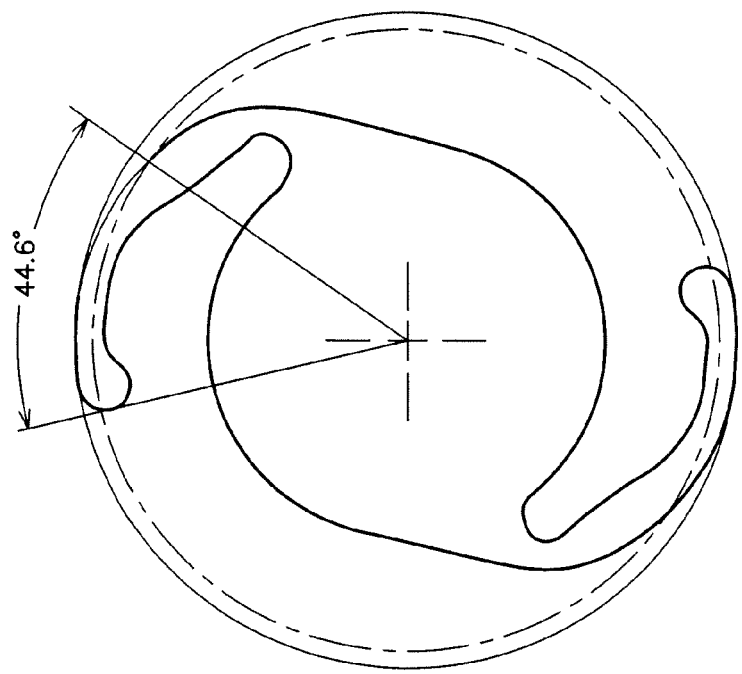
FIG. 8 is a model representation of the prior art IOL of FIG. 2A in a capsular bag and the angle of contact.

One common shortcoming of hydrophobic acrylic IOLs presently available to patients is the relatively small angle of contact the haptics have with the lenticular capsular bag. This results in multiple problems encountered by the surgeon during implantation of such a lens. First, a relative stiff haptic that exhibits relatively localized bending at a structurally designed elbow can lead to the puncturing of the posterior capsule upon implantation of the IOL in the capsular bag. As shown in FIGS. 2A and 2B, the haptics 40 include a structurally designed elbow 42. Following implantation of the IOL the diametrically inward force placed on the distal end 44 of the haptic by the capsular bag causes the haptic to bend predominantly at the designed elbow 42. The structured elbow design limits the degrees of mechanical freedom by which the haptic 40 can conform to the spherical shape of the capsular bag. The result is a relatively small angle of contact between the haptic 40 and the capsular bag as shown in FIG. 8 and FIG. 9, respectively.

A second problem encountered by the surgeon is the localized stretching and twisting of the capsular bag that is believed to be caused by the stiff-arm haptics of the prior art IOLs of FIGS. 2A and 2B. This localized stretching and twisting can cause the posterior capsule to wrinkle, and the wrinkles can cause unwanted visual affects. In contrast, the haptics of the IOLs described herein are designed to conform to the shape of the capsular bag, which allows for a greater contact area between the haptics and the interior perimeter surface of the bag. The compression by the bag on the haptics is sufficient to stabilize the IOL, yet minimize localized stretching of the bag. Also, the delocalized contact between the haptics and the capsular bag minimizes the amount of uneven stretching of the bag observed in the prior art IOLs.

Figure 3A:
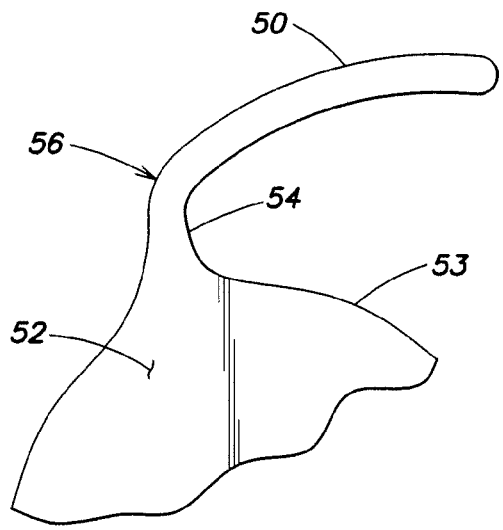
FIGS. 3A and 3B are representations of IOLs in the prior art.
Figure 3B:
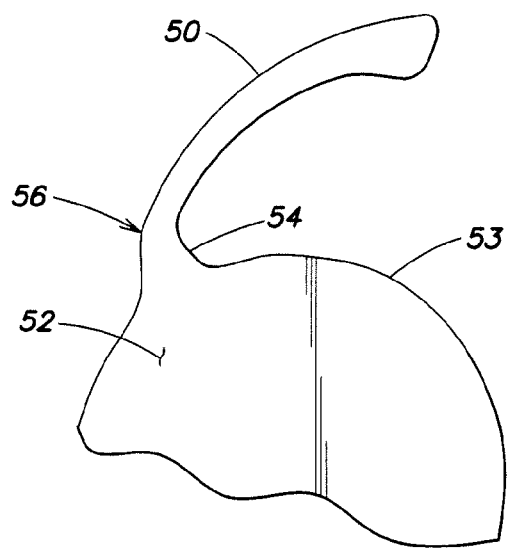

A third prior art hydrophobic IOL that is available to patients relies upon a structural bend in the haptic to essentially mimic the mechanical behavior of the structural elbow present in the two hydrophobic IOLs of FIGS. 2A and 2B. As shown in FIG. 3A and FIG. 3B a connection portion 54 of haptic 50 that integrates with the optic 52 has a relatively symmetrical top profile and projects nearly perpendicular from the optic peripheral edge 53. The haptic 50 then makes a sharp bend 56 and curves about the optic. In fact, the angle of contact for IOL of FIG. 3A is very similar to that of the IOL of FIG. 2A.

Applicants' IOL design provides a distinct shape or curvature to the haptics. The design provides a greater angle of contact between the haptics and the lenticular capsular bag of a human eye. As described, the haptics include a distal segment region and a deformation segment region. In a preferred embodiment, the haptics do not include a structurally designed elbow depicted in FIGS. 2A and 2B. Those in the art, however, do understand and recognize that an IOL of the invention can have a functional elbow, but the design of the elbow does not provide the lever-arm action exhibited by the haptics 40 of the IOLs in FIGS. 2A and 2B. By minimizing the functional importance of a structured elbow in the haptic design, Applicants essentially make available degrees of mechanical freedom along a greater contact length of the haptic that is not otherwise available with the traditional prior art designs. As a result, the haptics of the described IOLs will have a relatively large angle of contact between the haptics and the capsular bag. In most, if not all, instances, the described IOLs will have an angle of contact of not less than 50°, or not less than 52° and not greater than 70°.

Figure 4:
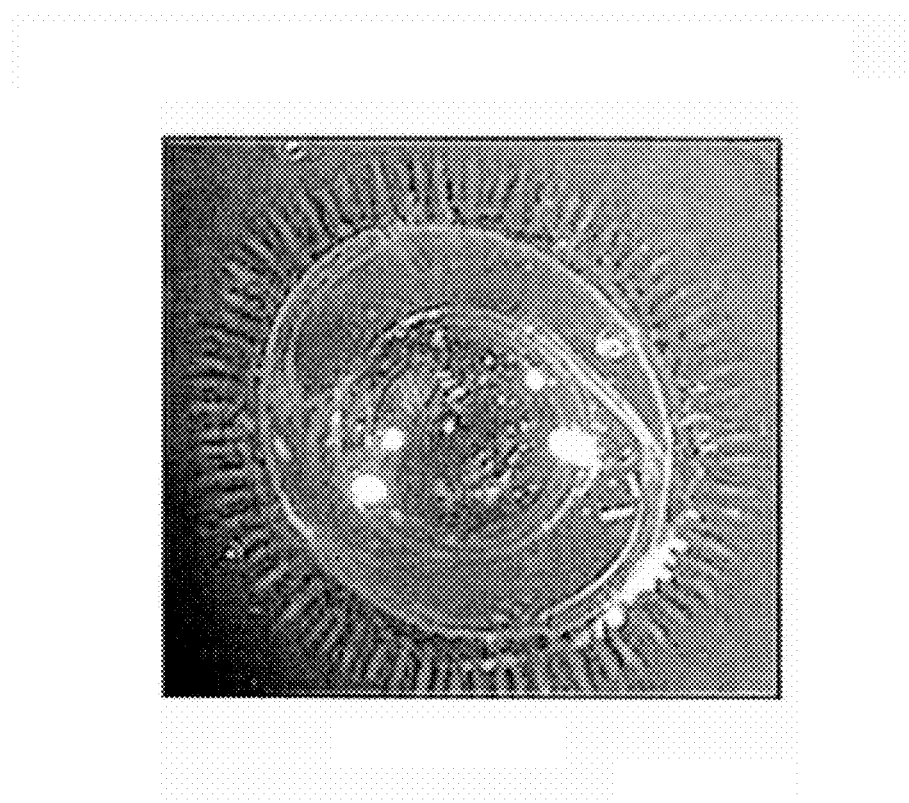
FIG. 4 is a photograph of an IOL of the invention implanted within a lenticular capsular bag of a human eye.

The design shape or curvature of the haptics in relation to the optic portion is important in establishing an angle of contact between the haptics and the interior perimeter region of a lenticular capsular bag in a human eye. By maximizing the angle of contact one can provide an implanted IOL with greater positional stability as well as with the propensity of the IOL to self-center within the capsular bag following implantation. An IOL of the invention that was implanted within the lenticular capsular bag of a human eye is shown in FIG. 4. As shown, the angle of contact between the haptics and the capsular bag essentially extends over the majority of the distal segment region and much of the deformation segment region of the haptics. One of skill would also notice from FIG. 4 a very slight stretching of the capsular bag that is in contact with the haptics, and that the stretching of the bag extends evenly over a greater haptic length—features that are not observed in any one of the prior art IOLs described. Again, by maximizing or extending the angle of contact over a greater area along the length of the haptics, Applicants have designed an IOL with greater positional stability and with an "auto-centering" feature not found in other IOLs to date.

In reference to FIG. 1, an unstressed IOL 10 can begin with the design of the distal segment region 20 of the haptics 16. The term "unstressed" IOL refers to an IOL that does not have any external compression or tension forces on the IOL. Essentially, an unstressed IOL can be described as an IOL placed on a bench top or stored in an IOL package. The distal segment region 20 is scribed by a distal segment angle α of 20° to 30° having a segment origin 26. One vector of segment angle α extends from the segment origin 26 to the distal endpoint 24, and the corresponding vector extends to the proximate endpoint 22. Accordingly, the region of haptic 16 including and between these two endpoints is the distal segment region.

Figure 5:
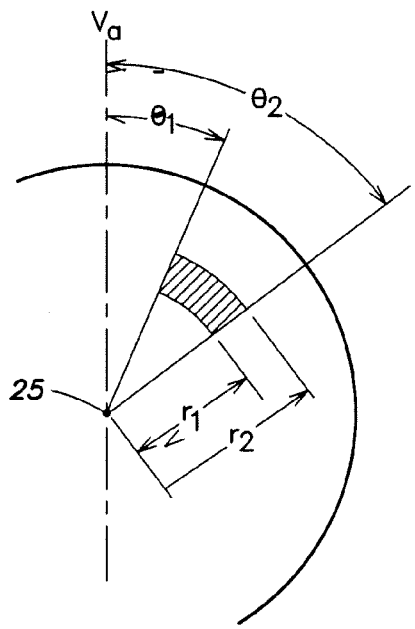
FIG. 5 is a geometric representation of a radial segment.

The segment origin 26 lies within a radial segment having a radial distance 28 of 1.5 mm to 1.9 mm from an optic center. The optic center 25 is the center origin of the optic portion 12 of an unstressed IOL. Referring to FIG. 5, the radial segment is bound by segment angles $\theta_1$ and $\theta_2$ of 30° and 45° from a vertical axis $V_a$. As shown, the vertical axis extends through a distal endpoint 24 of a distal segment region 20 of at least one haptic 16 and the optic center 25. The described radial segment is also bound by radial distances $r_1$ and $r_2$.

The intraocular lens 10 also includes a deformation segment region 30 that is bound by a proximate deformation endpoint 32 on an outer surface of the haptic 16 and the proximate endpoint 22 of the distal segment region 20. The deformation segment region 30 is scribed by a deformation segment angle β of 20° to 40° from the segment origin 26. One vector of segment angle β extends from the segment origin 26 to the proximate endpoint 24 of the distal segment, and the corresponding vector extends to the proximate deformation endpoint 32.

In one embodiment, the segment origin lies within a radial segment having a radial distance $r_1$ and $r_2$ of 1.6 mm to 1.8 mm, respectively, from the optic center. The radial segment is also bound by segment angles $\theta_1$ and $\theta_2$ of 33° to 40°, respectively, from the vertical axis. Also, the distal segment angle α is from 20° to 30°, and the deformation segment angle β is from 20° to 32°

In another embodiment, the segment origin lies within a radial segment having a radial distance $r_1$ and $r_2$ of 1.62 mm to 1.74 mm, respectively, from the optic center. The radial segment is also defined by segment angles $\theta_1$ and $\theta_2$ of 34° to 39°, respectively, from the vertical axis. Also, the distal segment angle α is from 22° to 28°, and the deformation segment angle β is from 22° to 30°.

In still another embodiment, the segment origin lies within a radial segment having a radial distance $r_1$ and $r_2$ of 1.65 mm to 1.72 mm, respectively, from the optic center. The radial segment is also defined by segment angles $\theta_1$ and $\theta_2$ of 35° to 38°, respectively, from the vertical axis. Also, the distal segment angle α is from 24° to 26°, and the deformation segment angle β is from 23° to 27°.

To best fit the inner perimeter surface of the lenticular capsular bag the outer surface of the distal segment region is preferably arcuate with a radius of curvature of 4.3 mm to 5.7 mm Likewise, the outer surface of the deformation segment region is preferably arcuate with a radius of curvature of 4.3 mm to 5.7 mm. Also, to maintain sufficient flexibility to conform to the inner perimeter surface of the capsular bag at least 80% of the distal segment region and at least 70% of the deformation segment region will preferably have a constant width Wh of from 0.25 mm to 0.65 mm, from 0.30 mm to 0.55 mm, or from 0.35 mm to 0.50 mm Also, the polymeric material comprising the haptics will preferably have a tangent modulus of elasticity of from 2 MPa to 6 MPa. The cross-sectional profile of the haptics 16 can be any shape though a rectangular shape is preferred with Wh having the shorter dimension.

The term "tangent modulus of elasticity" refers to the slope of the stress-strain diagram at 10% strain. Also, the methods and instruments used to determine a tangent modulus of elasticity for a particular material, particularly a polymeric material, is well known and understood by those in the art.

Figure 6:
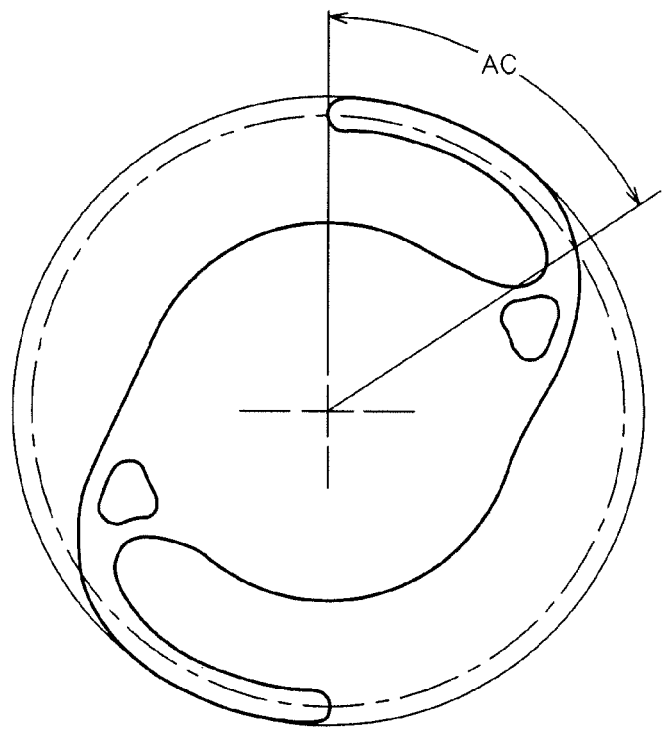
FIG. 6 is a model representation of an IOL of the invention with a large angle of contact.

As stated, the haptic is designed to maximize the angle of contact between the haptic, particularly, the distal segment region and the distal portions of the deformation segment region, and the lenticular capsular bag. As shown in FIG. 6, corresponding portions of the distal segment region and deformation segment region combine to form a contact region with an angle of contact AC of not less than 50° with the lenticular capsular bag of a human eye when the haptics are stressed following implantation of the lens into the capsular bag. In one embodiment, the angle of contact AC is not less than 52° and not greater than 70°.

Figure 7A:
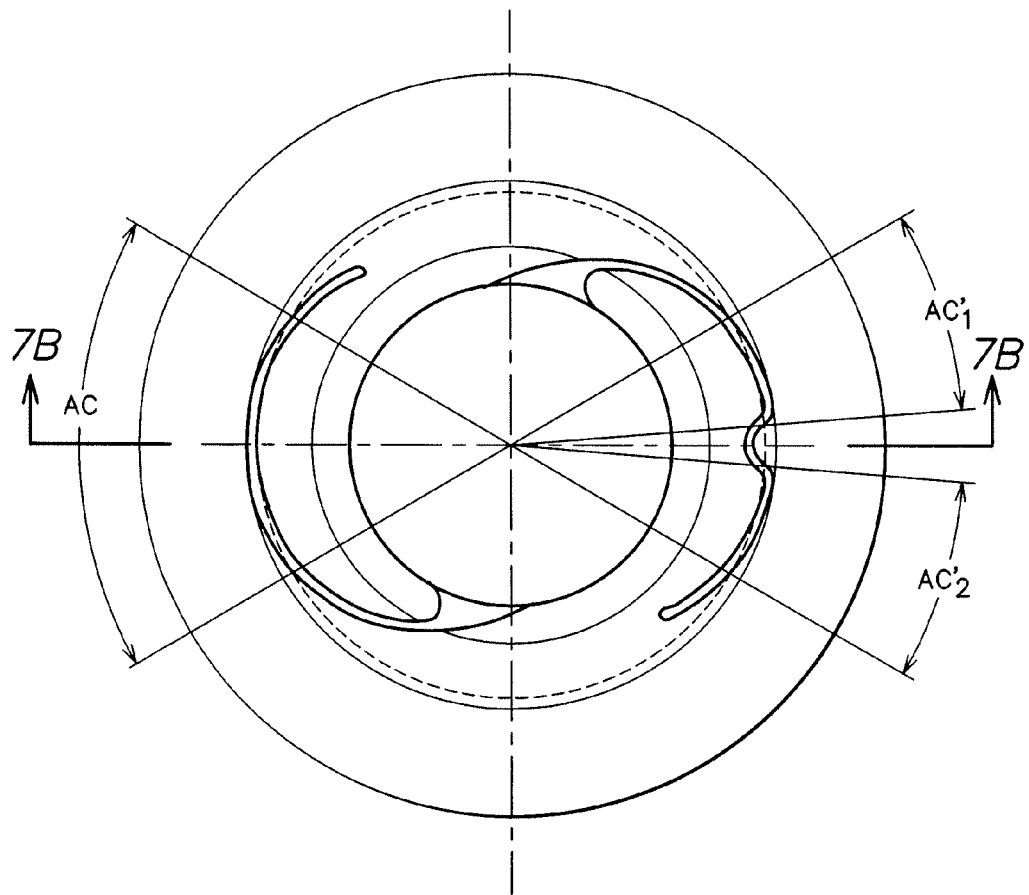
FIG. 7A is schematic top-view representation of an IOL within the arcuate jaws of a model used to determine the angle of contact the haptics have with a lenticular capsular bag.
Figure 7B:
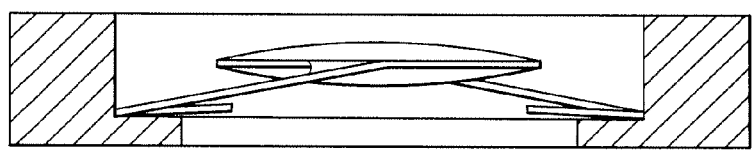
FIG. 7B is schematic side-view representation of an IOL within the arcuate jaws of the model of FIG. 7A.

The angle of contact can be measured directly from a lens per the instructions provided in ISO 11979-3. FIGS. 7A and 7B are schematic representations of the mechanical model used to model the lenticular capsular bag of a human eye. If a physical lens is not available, the angle of contact can be calculated by using a finite element model of compression based on the same ISO standard. The finite element method is a numerical technique for finding approximate solutions of partial differential equations, and several commercially available software packages (ANSYS™, Abaqus™, Nastran™, etc.) utilize the finite element method to solve for strains incurred in solid bodies due to applied loads and constraints.

To determine the angles of contact for the prior art IOLs the software package Abaqus™ has been utilized to approximate a solid model of an intraocular lens with finite elements and to apply compression of the outer diameter of the lens down to 10 mm per ISO 11979-3. An image of the compressed lens is exported from Abaqus™ and subsequently scaled and analyzed with a separate software package, SolidWorks™. The intersection points of the outer haptic edge and an arc offset 0.05 mm from the outer 10 mm compression fixture are located. The angular distance between these two points is then measured; this value represents the contact angle of the lens. In creating the finite element model of a given intraocular lens, e.g., a prior art IOL, the lens geometry can be obtained from issued patents containing graphics and dimensional details or by measurements taken directly from the lens.

Figure 11:
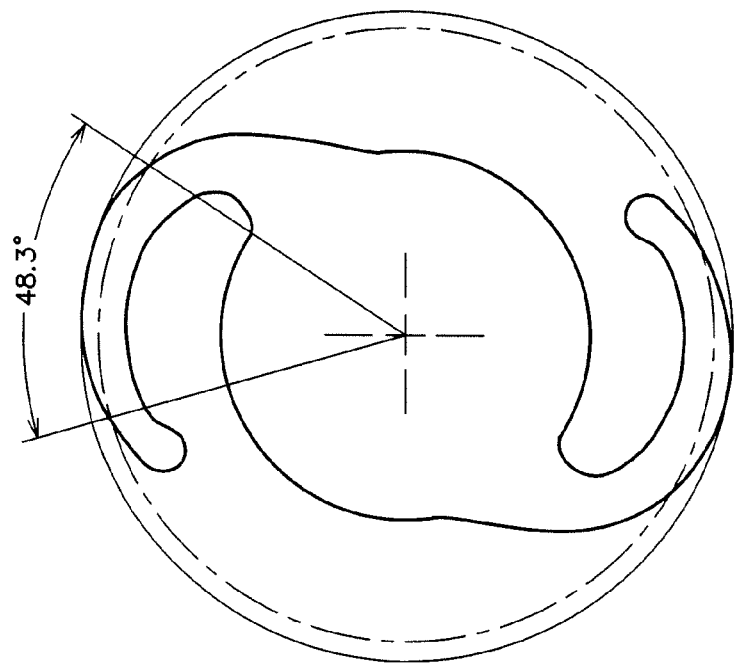
FIG. 11 is a model representation of another prior art IOL in a capsular bag and the angle of contact.
Figure 10:
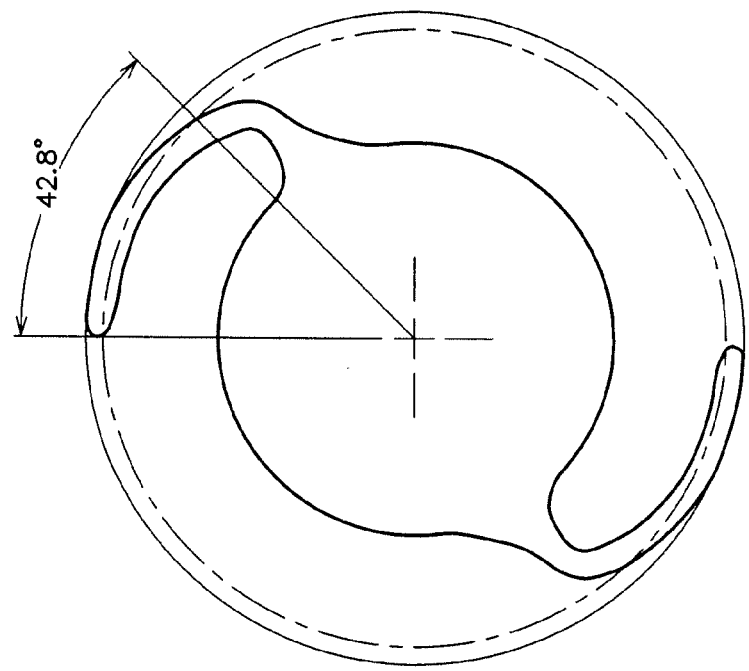
FIG. 10 is a model representation of the prior art IOL of FIG. 3A in a capsular bag and the angle of contact.

The angles of contact for each of the prior art IOLs described herein are determined using the model described. The angle of contact in each of the prior art IOLs described is less than about 48°. As indicated in FIGS. 9, 10 and 11, the angle of contact for the prior art IOLs of FIGS. 2A, 2B and 4 were determined using the mathematical software programs identified above. The three described prior art IOLs are all one-piece IOLs formed from a single hydrophobic copolymer. The term "hydrophobic copolymer" is defined as a copolymer with an equilibrated water content of less than 5% by weight. A fourth prior art IOL depicted in FIG. 11 is formed of a hydrophilic copolymer with a water content of about 28% by weight. The angle of contact for each of the prior art IOLs are listed in Table 1 below.

TABLE 1

| Prior Art IOLs: Angle of Contact | | | |
|---|---|---|---|
| FIGS. 2A/8 | FIGS. 2B/9 | FIGS. 4/10 | FIG. 11 |
| 44.6° | 38.1° | 42.8° | 48.3 |

As one might expect, the physical contact between the haptics and the inner perimeter surface of the capsular bag following implantation of an IOL of the invention causes the haptics, particularly, the distal segment region of the haptics, to move inward toward the optic center of the IOL. In fact, once implanted in the capsular bag of a human eye the segment origin translates to a point within a radial distance of 0.3 mm or less from the optic center. Ideally, the segment origin would actually translate to the optic center. In any case, the segment origin moves inward toward the optic center following implantation of the IOL to a radial distance of 0.3 mm or less, 0.2 mm or less or 0.1 mm or less, from the optic center.

In reference to the model used to determine angles of contact, as the distal segment region of the haptics moves inward toward the optic center as the arcuate jaws close upon the IOL the IOL the segment origin translates to a point within a radial distance of 0.3 mm or less from the optic center. Ideally, the segment origin would actually translate to the optic center. In any case, the segment origin moves inward toward the optic center following implantation of the IOL to a radial distance of 0.3 mm or less, 0.2 mm or less or 0.1 mm or less, from the optic center, in accordance with ISO Test No. 11979-3(2006).

Figure 12C:
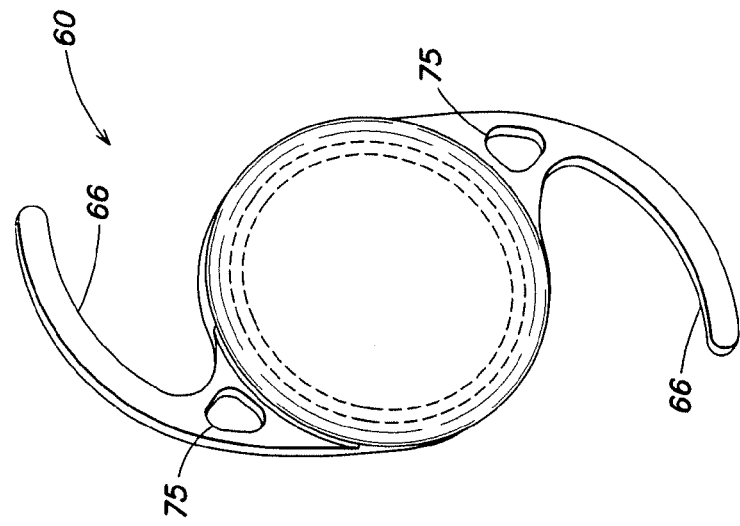
FIG. 12C is a posterior view of the IOL of FIG. 12A.
Figure 12B:
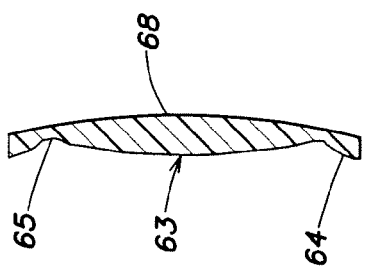
FIG. 12B is a cross-sectional view of the IOL of FIG. 12A.
Figure 12A:
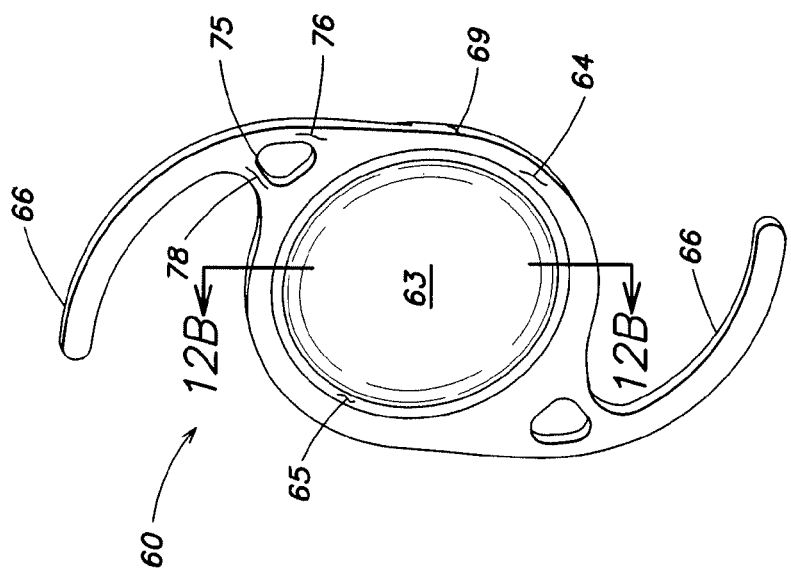
FIG. 12A is an anterior view of an IOL of the invention.

In one embodiment, and as shown in FIG. 12A, the optic portion of IOL 60 includes an anterior face with a central optical zone 63, a peripheral zone 64 entirely surrounding the optical zone, a recessed annular zone 65 that is disposed posterior to the peripheral zone 64 and an optic peripheral edge 69. The IOL shown in FIG. 12A also includes an integration region of a haptic 66 having an opening 75 thereby forming an outer integration member 76 and an inner integration member 78. The haptic 66 of IOL 60 will exhibit an angle of contact of not less than 50°, or not less than 52° and not greater than 70°, with the lenticular capsular bag of a human eye when the haptic is stressed following implantation of the lens into the capsular bag. FIG. 12B is a cross-sectional view of the optic portion of the IOL of FIG. 12A showing the anterior face with the central optical zone 63, peripheral zone 64, and the recessed annular zone 65. The posterior optical zone 68 is also shown. FIG. 12C is a posterior view of the IOL of FIG. 12A showing the posterior optical zone 68.

Figure 13:
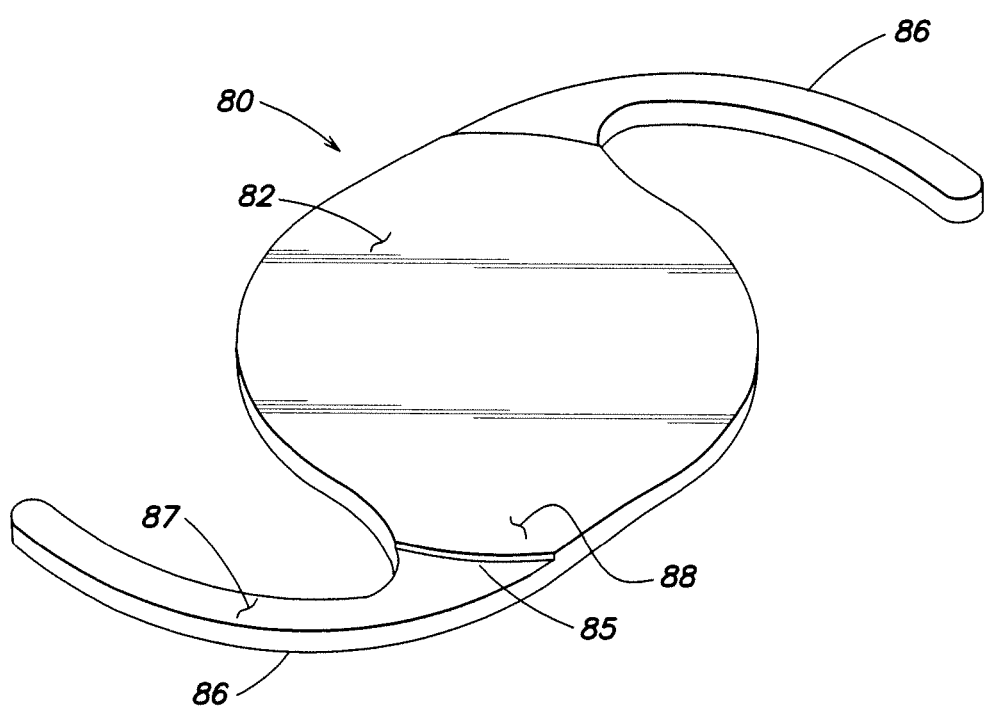
FIG. 13 is a posterior view of an IOL of the invention.

As shown in FIG. 13, in addition to the anterior optical features described and shown in FIGS. 12A, 12B and 12C, an IOL 80 includes a posterior optical zone 82, and the at least two haptics 86 can include a distal posterior face 87, a proximal posterior face 88, and a step face 85 disposed at a boundary therebetween. The distal posterior face 88 may be substantially perpendicular to the optical axis or disposed at an angle relative to a plane perpendicular to the optical axis. The haptics 86 of IOL 80 will exhibit an angle of contact of not less than 50°, or not less than 52° and not greater than 70°, with the lenticular capsular bag of a human eye when the haptics are stressed following implantation of the lens into the capsular bag.

In one embodiment, the optic portion of each lens will have an optic diameter from 5.7 mm to 4.5 mm. The optic diameter of the IOL will of course depend upon the optical power of the lens. IOLs of less optical power, e.g., a 15 diopter lens, will typically have a larger optic diameter than an IOL with greater optical power, e.g., a 30 diopter lens. A given range of exemplary optic diameters for the IOLs is provided in Table 2.

TABLE 2

| power (diopter) | optic diameter (mm) |
|---|---|
| 15-18 | 5.7-5.1 |
| 17-23 | 5.5-4.8 |
| 21-26 | 5.4-4.5 |
| 24-30 | 5.1-4.5 |

In one embodiment, the optic portion of each IOL will have a center thickness that deviates no more than 15% from an average center thickness across an optical power range of from 18 to 23 diopters. Also, the cross-sectional area of any one optic portion deviates no more than 6%, or no more than 4%, from an average cross-sectional area across the optical power range of 18 to 23 diopters. An exemplary sized optic portion of an IOL with a refractive power of 19 diopters to 22 diopters will have an optic center thickness of 0.50 mm to 0.60 mm and a nominal cross-sectional area of 2.1 mm$^2$ to 2.7 mm$^2$.

The optic portion of the intraocular lens can also include a toric optical zone (commonly referred to as a "toric IOL"). A topic IOL can provide the functional requirements of a lens as well as correct refractive abnormalities of an eye associated with corneal astigmatism. The toric optical zone provides cylindrical correction to compensate for astigmatism. Also, because astigmatism is usually associated with other refractive abnormalities, such as myopia (nearsightedness) or hypermetropia (farsightedness), toric IOLs can be prescribed with a spherical correction to correct myopic astigmatism or hypermetropic astigmatism. A toric optical surface is formed on either the posterior lens surface (to achieve a "back surface toric JUL") or the anterior lens surface (to form a "front surface tonic IOL").

The positional stability and self-centering characteristic of the described IOLs becomes very important in the designing of a toric IOL. As stated, the unique stabilizing features provided by the haptics inhibit rotation of the lens within the capsular bag following implantation. In other words, following proper axial alignment of a toric IOL by a surgeon the cylindrical axis of the toric zone remains generally aligned with the axis of the astigmatism years after implantation.

A prescription for a toric IOL will typically specify refractive power, and spherical correction and cylindrical correction in relation to a base axis. Toric IOLs prescriptions are generally offered in 5° or 10° increments ranging from 0° to 180°. The toric optical zone is easily machined into the posterior or anterior surface of the optic portion of the IOL using methods well known in the optical art. Also, those of ordinary skill in the art would know how to diagnose and prescribe a toric IOL according to the specific visual corrective needs of each patient.

One advantage of having an opening 75 in at least one haptic 77 depicted in FIG. 8 is that the surgeon can easily rotate the IOL following the implantation of the lens by positioning a rotating tool into the opening and rotating the lens within the capsular bag to the proper axial alignment. Again, the positional stability and self-centering characteristics of the described IOLs makes this possible and quite feasible.

One embodiment is directed to an intraocular lens comprising an optic portion and two haptics, and each haptic is integrated to a peripheral edge of the optic portion by a haptic integration region. The optic portion, the two haptics and the haptic integration regions are each formed of a hydrophobic polymeric material having a tangent modulus of elasticity of from 2 Mpa to 6 MPa. Each of the haptics comprise a distal segment region and a deformation segment region. The distal segment region has an outer distal length bounded by a proximate and a distal endpoint on an outer surface of the haptic, and is scribed by a distal segment angle α of 20° to 30°. The distal segment angle has a segment origin that extends a radial distance of 1.5 mm to 1.9 mm from an optic center and a segment angle θ of from 34° to 40° from a vertical axis. The vertical axis extends through the distal endpoint of at least one of the two haptics and the optic center. The deformation segment region has an outer deformation length bounded by a proximate deformation endpoint on an outer surface and the proximate endpoint of the corresponding distal segment region, and is scribed by a deformation segment angle β of 20° to 40° from the segment origin.

The Optical, Polymeric Materials

The haptic design principles described above can be applied to a wide variety of optical polymeric materials. Non-limiting examples of such materials include those known to be used in IOLs. For example, the method of the present invention can be applied to siloxy-containing copolymers, acrylic copolymers, hydrophilic copolymers or hydrophobic copolymers. The terms polymer and copolymer are used interchangeably, and it is well understood by those of skill in the art that a copolymer is prepared from more than one monomeric component.

In one embodiment, a copolymeric material that can be used to make an IOL described herein will be hard enough to machine at room temperature, and one which is foldable through a controlled hydrating process. The IOL may be hydrated to a suitably flexible state with minimal water uptake. The relatively low water uptake allows efficient hydration without affecting mechanical or optical properties and results in little, if any, change in the dimensions or the refractive index of the lens. One exemplary copolymer with the features or properties described can include: a) a first monomeric component that is selected from an aryl acrylate or an aryl methacrylate; b) a second monomeric component which is a monomer having an aromatic ring with a substituent having at least one site of ethylenic unsaturation, and c) a third monomeric component which is a high water content hydrogel-forming monomer. The copolymer can further include a crosslinking agent.

The IOLs described can include a copolymer comprising: a) at least about 20% by weight of a first monomeric component selected from the group consisting of ethylene glycol phenyl ether acrylate and polyethylene glycol phenyl ether acrylate; b) at least about 10% by weight of a second monomeric component selected from the group consisting of substituted styrene and unsubstituted styrene; c) at least about 10% by weight of a third monomeric component selected from the group consisting of hydroxy ethyl methacrylate, hydroxyethoxy ethyl methacrylate, and methacrylic acid; d) less than about 10% by weight percent of a crosslinking agent selected from the group consisting of a diacrylate and a dimethacrylate. Also, the copolymer will have a refractive index greater than about 1.50 and is foldable at normal room temperature when hydrated, and is machinable at about room temperature when dry.

In another embodiment, the intraocular lens comprises a cured copolymer that is prepared from a cationically polymerizable, branched alkene monomer, and a monomer that includes a pendent benzocyclobutene group (herein called "BCB group"), The cationically polymerizable branched alkene monomer preferably contains a tertiary carbon on the vinyl group in the alkene. As known by those of skill in the art, tertiary carbocations are relatively stable due to the electron-density of the surrounding carbons that stabilize the positive charge of the cation. Polyisobutylene, a preferred branched alkene monomer, as discussed above, is an example of an alkene monomer polymerizable by cationic chemical means that contains a tertiary carbon. Molecules such as propene contain secondary carbons at the vinyl group and, as known by those of skill in the art, are not cationically polymerized.

Due to the strained four-membered ring, the BCP group is converted to oxylylene at temperatures greater than 180° C. At such elevated temperatures, the BCB group undergoes Diels-Alder reactions with dienophiles to form a six-membered ring, or reacts with itself to form an eight-membered ring. Polymers containing multiple pendant BCB groups per molecular chain can be thermally crosslinked with or without dienophiles. Each crosslink consists of a ring structure of carbon-carbon bond, which is more thermally stable than the sulfur bridge in vulcanized polymers and is stronger than the Si—O bond in silicone copolymers. The BCB crosslinking only involves heat. As long as the polymer is stable at the crosslinking temperature, there is no toxic chemical involved in order to from a cured crosslinked copolymer.

The monomer having a BCB group can be any monomer containing at least one BCB-functional moiety. It is preferred that the monomer be cationically polymerizable and be compatible with the branched alkene monomer. In one embodiment, the monomer having a BCB group has the formula

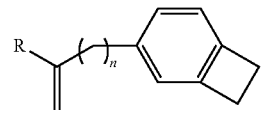

wherein R is hydrogen or an alkyl group and n is an integer selected from 0, 1, 2 or 3. Suitable monomers having a BCB group include 4-vinylbenzocyclobutene, 4-(α-alkylvinyl) benzocyclobutenes such as 2-(4-benzocyclobutenyl)-propene and 2-(4-benzocyclobutenyl)-1-butene, and 4-(2-methyl-alkenyl)benzocyclobutenes such as 2-methyl-3-(4-benzocyclobutenyl)-1-propene and 2-methyl-4-(4-benzocyclobutenyl)-1-butene.

Like the branched alkene, the monomer having a pendant benzocyclobutene (BCB) group should also be cationically polymerizable. Olefins having a secondary carbon on the vinyl group are cationically polymerizable in instances when the electronegativity of the aromatic ring adjacent to the vinyl group can stabilize the carbocation. Thus, monomer olefins such as 4-vinylbenzocyclobutene can be cationically polymerized, and easily incorporated into the polymer simply by titrating it into the reaction during its polymerization. This is different than, for example, the allyl-BCB, which cannot be added to a cationic polymerization, in part because the aromatic ring in the BCB is not adjacent to the vinyl group.

BCB-type monomers having and a tertiary carbon on the vinyl group are also suitable for cationic polymerization even if the vinyl group is not adjacent to the aromatic ring of the BCB. Tertiary carbons, which become quaternary carbons during polymerization, are stabilized by the electronegativity of the surrounding carbons. Therefore, monomers having tertiary carbons on the vinyl carbons can be incorporated into a cationic polymerized reaction much in the same manner as the alkene having a tertiary carbon is incorporated. 2-Methyl-3-(4-benzocyclobutenyl)-propene is an example of this type of compound. Also preferred are monomers that draw on the electronegativity of both the surrounding carbons and the aromatic ring, for example 2-(4-benzocyclobutenyl)-propene. These type of monomers will cationically polymerize as they are stabilized both by the methyl group (as in this case of 2-(4-benzocyclobutenyl)-propene) and the aromatic ring.

In another embodiment, the optical polymeric material can be prepared as a copolymer from at least three monomeric components. The first monomeric component is present in the copolymer in an amount of at least 70% by weight, and its homopolymer will have a refractive index of at least 1.50, preferably at least 1.52 or at least 1.54. The second monomeric component is present in the copolymer in an amount from 3% to 20% or from 3% to 10%, by weight, and its homopolymer will have a glass transition temperature of less than about 300° C., preferably less than about 220° C. The first and second monomeric components together represent at least 80% by weight of the copolymer. The term "homopolymer" refers to a polymer that is derived substantially completely from the respective monomeric component. Minor amounts of catalysts, initiators and the like can be included, as is conventionally the case, in order to facilitate the formation of the homopolymer.

Non-limiting examples of first and second monomeric components include polymers comprising units of $C_1$-$C_{10}$ alkyl methacrylates (e.g., methyl methacrylate, ethyl methacrylate, propyl methacrylate, butyl methacrylate, octyl methacrylate, or 2-ethylhexyl methacrylate; preferably, methyl methacrylate to control mechanical properties), $C_1$-$C_{10}$ alkyl acrylates (e.g., methyl acrylate, ethyl acrylate, propyl acrylate, or hexyl acrylate; preferably, butyl acrylate to control mechanical properties), $C_6$-$C_{40}$ arylalkyl acrylates (e.g., 2-phenylethyl acrylate, benzyl acrylate, 3-phenylpropyl acrylate, 4-phenylbutyl acrylate, 5-phenylpentyl acrylate, 8-phenyloctyl acrylate, or 2-phenylethoxy acrylate; preferably, 2-phenylethyl acrylate to increase refractive index), and $C_6$-$C_{24}$ arylalkyl methacrylates (e.g., 2-phenylethyl methacrylate, 3-phenylpropyl methacrylate, 4-phenylbutyl methacrylate, 2-phenoxyethyl methacrylate, 3,3-diphenylpropyl methacrylate, 2-(1-naphthylethyl)-methacrylate, benzyl methacrylate, or 2-(2-naphthylethyl) methacrylate.

Particularly useful first monomeric components include styrene, vinyl carbazole, vinyl naphthalene, benzyl acrylate, phenyl acrylate, 2-phenoxyethyl acrylate, 2-phenoxyethyl methacrylate and mixtures thereof. Particularly useful second monomeric components include n-butyl acrylate, n-hexyl acrylate, 2-ethylhexyl acrylate, 2-ethoxyethyl acrylate and mixtures thereof. The third monomeric component is best described as a cross-linking monomeric constituent that can form crosslinks with the first or the second monomeric components. Preferably, the cross-linking monomeric component is multi-functional and can chemically react with both the first and second monomeric components. Preferably, the third component is present in the copolymer in an amount of less than about 3% by weight of the copolymer. Examples of useful crosslinking monomeric components include ethylene glycol dimethacrylate, propylene glycol dimethacrylate, ethylene glycol diacrylate and the like and mixtures thereof.

The copolymer can further include a fourth component derived from a hydrophilic monomeric component. This fourth component is present in an amount, from 2% to 10% by weight of the copolymer. At times, and depending upon the hydrophobic lens material, the addition of a hydrophilic monomeric component can reduce the formation of water vacuoles, which can scatter light and cause what is referred to in the art as "glistenings".

In another embodiment, the optical, polymeric materials can also be prepared from monomers having the formula:

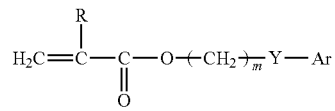

wherein:
R is H or $CH_3$; m is 0-10;
Y is nothing, O, S, or NR wherein R is H, $CH_3$, $C_nH_{2n+1}$ (n=1-10 iso $OC_3H_7$, phenyl or benzyl; Ar is any aromatic ring, such as benzene, which can be unsubstituted or substituted with H, $CH_3$, $C_2H_5$, n-$C_3H_7$, iso-$C_3H_7$, $OCH_3$, $C_6H_{11}$, Cl, Br, phenyl or benzyl; and a cross-linking monomer having a plurality of polymerizable ethylenically unsaturated groups. The optical material will have a glass transition temperature not greater than 37° C. and an elongation of at least 150%.

Exemplary monomers include, but are not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, and the like, including the corresponding methacrylates and acrylates.

The aryl acrylate/methacrylate based optical materials will generally comprise a greater mole percent of acrylate ester residues than of methacrylate ester residues. It is preferred that the aryl acrylate monomers constitute from about 60 mole percent to about 95 mole percent of the polymer, while the aryl methacrylate monomers constitute from about 5 mole percent to about 40 mole percent of the polymer. Most preferred is a polymer comprising about 60-70 mole percent 2-phenylethyl acrylate and about 30-40 mole percent 2-phenylethyl methacrylate.

In yet another embodiment, the optical, polymeric material can also be prepared by polymerizing the following monomeric components: (A) 5-25% by weight of acrylate represented by the general formula

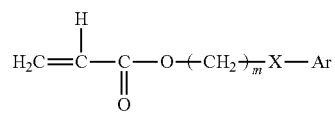

wherein Ar represents an aromatic ring of which hydrogen atom may be substituted by a substitutional group, X represents an oxygen atom or a direct bonding, and m represents an integer of 1 to 5; (B) 50 to 90% by weight of 2-hydroxyethyl (meth)acrylate; and (C) 5 to 45% by weight of a (meth) acrylate monomer though not of the formula that represent monomer (A) and not 2-hydroxyethyl (meth)acrylate. Also, the coefficient of water absorption of the homopolymer of monomer (C) is not more than 30% by weight.

In the present invention the coefficient of water absorption is defined as the following equation: water absorption (% wt)=(W−Wo)/Wo×100 wherein the value is calculated at 25° C. by using the specimen having 1 mm thickness at cutting, W represents a weight of the specimen in equilibrium state of water, and Wo represents a weight of the specimen in a dry state.

In each of the embodiments above, the optical, polymeric materials are prepared by generally conventional polymerization methods from the respective monomeric components.

I claim:

1. An intraocular lens comprising an optic portion having a peripheral edge and at least two haptics, each haptic integrated with the peripheral edge of the optic portion by a corresponding haptic integration region, each haptic comprising a distal segment region and a deformation segment region,
wherein the distal segment region has an outer distal length defined by a proximate endpoint and a distal endpoint on an outer surface of the haptic, the distal segment region scribed by a distal segment angle α of 200 to 300, and the outer surface of the distal segment region is arcuate with a radius of curvature of 4.3 mm to 5.7 mm, and
the deformation segment region has an outer deformation length bounded by a proximate deformation endpoint on an outer surface of the haptic and the proximate endpoint of the distal segment region, the deformation segment region scribed by a deformation segment angle β of 20° to 40°,
the distal segment angle and the deformation segment angle having a segment origin that lies within a radial segment bound by a radial distance 1.5 mm and 1.9 mm from an optic center and a segment angle θ of from 30° and 45° from a vertical axis, the vertical axis extending through the distal endpoint of at least one haptic and the optic center,
wherein a portion of the outer surface of the distal segment region and a portion of the outer surface of the deformation segment region combine to form an angle of contact of not less than 52° and not more than 70° with an arcuate jaw if the haptics are concentrically stressed to a jaw diameter of 10 mm in accordance with ISO Test No. 11979-3(2006).

2. The intraocular lens of claim 1 wherein at least 80% of the distal segment region and at least 70% of the deformation segment region have a constant width $W_H$ of from 0.25 mm to 0.65 mm.

3. The intraocular lens of claim 1 wherein the integration region comprises an opening thereby forming outer and inner integration members.

4. The intraocular lens of claim 1 wherein the distal segment angle is from 22° to 28°, and the segment origin extends the radial distance 1.6 mm to 1.8 mm from the optic center.

5. The intraocular lens of claim 1 wherein the radial segment is bound by a radial distance of 1.62 mm to 1.72 mm from the optic center, and the segment angle θ of 34° to 40° from the vertical axis.

6. The intraocular lens of claim 1 wherein a portion of the outer surface of the distal segment region and a portion of the outer surface of the deformation segment region combine to form an angle of contact of not less than 50° with a lenticular capsular bag of a human eye when the haptics are stressed following implantation of the lens into the bag.

7. The intraocular lens of claim 1 wherein the segment origin translates to an implanted radial distance of 0.3 mm or less from the optic center when the haptics are stressed following implantation of the lens into a lenticular capsular bag of a human eye.

8. The intraocular lens of claim 1 wherein the segment origin translates to an implanted radial distance of 0.3 mm or less from the optic center if the haptics are concentrically stressed in a model representation of a lenticular capsular bag of a human eye in accordance with ISO Test No. 11979-3 (2006).

9. The intraocular lens of claim 1 formed as a one-piece, polymeric material with a tangent modulus of elasticity of from 2 MPa to 6 MPa.

10. The intraocular lens of claim 1 wherein the optic portion comprises an anterior face and a substantially opposing posterior face, wherein the anterior face includes a central face, a peripheral face and an annular face, the annular face posteriorly recessed between the central face and the peripheral face.

11. A one-piece intraocular lens comprising an optic portion and two haptics, each haptic integrated to a peripheral edge of the optic portion by a haptic integration region, and the optic portion, the two haptics and the haptic integration regions each comprise a polymeric material having a tangent modulus of elasticity of from 2 MPa to 6 MPa, wherein
each of the haptics comprise a distal segment region and a deformation segment region, wherein the distal segment region has an outer distal length bounded by a proximate and a distal endpoint on an outer surface of the haptic, the distal segment region scribed by a distal segment angle α of 20° to 30°, the distal segment angle having a segment origin that lies within a radial segment bound by a radial distance of 1.5 mm and 1.9 mm from an optic center and a segment angle θ of 34° and 40° from a vertical axis, the vertical axis extending through the distal endpoint of at least one of the two haptics and the optic center, and
each of the deformation segment regions has an outer deformation length bounded by a proximate deformation endpoint on an outer surface and the proximate endpoint of the corresponding distal segment region, the deformation segment region scribed by a deformation segment angle β of 20° to 40° from the segment origin, and
a portion of the outer surface of the distal segment region and a portion of the outer surface of the deformation segment region combine to form an angle of contact of not less than 52° and not more than 70° with an arcuate jaw, and the segment origin translates to a point within 0.3 mm or less of a radial distance from the optic center, if the haptics are concentrically stressed to a jaw diameter of 10 mm in accordance with ISO Test No. 11979-3(2006).

12. The intraocular lens of claim 11 wherein the distal segment angle α is from 22.5° to 27.5°, the segment origin extends 1.6 mm to 1.8 mm radially from the optic center, and the outer surface of the distal segment region is arcuate with a radius of curvature of 4.6 mm to 5.4 mm.

13. The intraocular lens of claim 11 wherein corresponding portions of the outer surfaces of the distal segment region and deformation segment region combine to form an angle of contact of not less than 52° and not more than 70° with a lenticular capsular bag of a human eye when the haptics are stressed following implantation of the lens into the bag.

14. The intraocular lens of claim 11 wherein the optic portion has a refractive power of 19 diopters to 22 diopters, an optic center thickness of 0.50 mm to 0.60 mm and a nominal cross-sectional area of 2.1 $mm^2$ to 2.7 $mm^2$.

15. A one-piece intraocular lens comprising an optic portion with an optic center and at least two haptics, each haptic integrated to a peripheral edge of the optic portion by a haptic integration region, and each of the haptics comprise a distal segment region ending with a distal endpoint on an outer surface of the haptic and a deformation segment region beginning with a proximate deformation endpoint on the outer surface of the haptic, wherein the distal endpoint and the proximate deformation segment endpoint are further defined by a sum of a distant segment angle α and a deformation segment angle β and a segment origin that is 1.5 mm and 1.9 mm from the optic center if the intraocular lens is unstressed,
wherein upon applying a concentric stress to the intraocular lens with an arcuate jaw to a diameter of 10 mm in accordance with ISO Test No. 11979-3(2006) a portion of the distal segment region and a portion of the deformation segment region combine to form an angle of continuous contact of not less than 52° and not more than 70° with the arcuate jaw, and the segment origin translates to an implanted radial distance of 0.3 mm or less from the optic center.

16. The intraocular lens of claim 15 wherein the optic portion comprises an anterior face and a substantially opposing posterior face, wherein the anterior face includes a central face, a peripheral face and an annular face, the annular face posteriorly recessed between the central face and the peripheral face.

17. The intraocular lens of claim 15 wherein the optic portion and the at least two haptics comprises of a polymeric material with a tangent modulus of elasticity of from 2 MPa to 6 MPa.

18. The intraocular lens of claim 16 wherein the optic portion has a refractive power of 19 diopters to 22 diopters, an optic center thickness of 0.50 mm to 0.60 mm and a nominal cross-sectional area of 2.1 $mm^2$ to 2.7 $mm^2$.

19. The intraocular lens of claim 1 wherein the outer surface of the deformation segment region is arcuate with a radius of curvature of 4.3 mm to 5.7 mm.

20. The intraocular lens of claim 1 wherein the distal segment angle is from 24° to 26°, and the segment origin extends the radial distance 1.65 mm to 1.72 mm from the optic center.

21. The intraocular lens of claim 15 wherein the radial segment is bound by the radial distance of 1.6 mm to 1.8 mm from the optic center, and the segment angle θ of 33° to 40° from the vertical axis.

22. The intraocular lens of claim 1 wherein the radial segment is bound by the radial distance of 1.62 mm to 1.74 mm from the optic center, and the segment angle θ of 34° to 39° from the vertical axis.

23. The intraocular lens of claim 15 wherein the radial segment in the unstressed lens is bound by the radial distance of 1.6 mm to 1.8 mm from the optic center.

* * * * *